United States Patent [19]

Cholet

[11] Patent Number: 4,651,557
[45] Date of Patent: Mar. 24, 1987

[54] APPARATUS FOR MEASURING THE FLOW-PRESSURE CHARACTERISTICS OF THE GAS PASSING THROUGH A PRODUCT SAMPLE HAVING TWO FACES

[75] Inventor: Georges Cholet, Orleans, France

[73] Assignee: Societe Nationale d'Exploitation Industrielle des Tabacs et Allumettes, France

[21] Appl. No.: 807,816

[22] Filed: Dec. 11, 1985

[30] Foreign Application Priority Data

Dec. 19, 1984 [FR] France ............... 84 19434

[51] Int. Cl.⁴ ........................... G01N 15/08
[52] U.S. Cl. ............................. 73/38
[58] Field of Search ...................... 73/38, 37.7

[56] References Cited

U.S. PATENT DOCUMENTS

| 3,371,518 | 3/1968 | Keyes | 73/38 |
| 3,466,925 | 9/1969 | Ziegenhagen et al. | 73/38 |
| 3,720,095 | 3/1973 | Molins | 73/38 |
| 4,191,046 | 3/1980 | Baker et al. | 73/38 |
| 4,198,853 | 4/1980 | Graham et al. | 73/38 |
| 4,311,037 | 1/1982 | Gotchel et al. | 73/38 |
| 4,462,248 | 7/1984 | Cronshaw | 73/38 |
| 4,471,649 | 9/1984 | Cronshaw | 73/38 |
| 4,480,463 | 11/1984 | Schumacher et al. | 73/38 |
| 4,495,796 | 1/1985 | Hester | 73/38 |

FOREIGN PATENT DOCUMENTS 2132366 7/1984 United Kingdom .

Primary Examiner—Michael J. Tokar
Assistant Examiner—Joseph W. Roskos
Attorney, Agent, or Firm—Jacobs & Jacobs

[57] ABSTRACT

An apparatus is provided for measuring the flow-pressure characteristics of a gas passing through a product sample with two faces, for example for measuring the permeability of a sample of air permeable material such as cigarette paper. A sample holder allows the external face of the paper to be exposed to atmospheric pressure and the internal face to a sub-atmospheric pressure created by a pump, whereas the value of this pressure difference and of the air flow passing through the sample is measured. A control system comprising a continuously controlled control valve and an electronic circuit controlled by a reference signal and a signal representative of the real pressure difference or of the real flow rate allows measurement conditions to be obtained rapidly in conformity with the requirements of certain standards and recommendations.

6 Claims, 4 Drawing Figures

APPARATUS FOR MEASURING THE FLOW-PRESSURE CHARACTERISTICS OF THE GAS PASSING THROUGH A PRODUCT SAMPLE HAVING TWO FACES

BACKGROUND OF THE INVENTION

1. Field of the Invention

The present invention relates to an apparatus for measuring the flow-pressure characteristics of a gas passing through a product sample with two faces, comprising a sample holder adapted so that one of the faces of the sample is subjected to the atmospheric pressure, a pump for applying a sub-atmospheric pressure on the other face of the sample, a sensor for measuring the pressure differential, á sensor for measuring the gas flow through the sample which results from said pressure differential, a reference signal generator and means for comparing the output of one of the two sensors and the output of the reference signal generator.

Such an apparatus is in particular used for measuring the permeability to air of materials used as cigarette paper, or sleeving for filters, in compliance for example with the international standard ISO 2965 or with the French standard NF V37-010. The permeability is the ratio of the air flow (volume per unit of time) per unit of surface of the sample to the pressure difference through this sample.

2. Description of the Prior Art

The British patent application No. 2 094 986A describes an apparatus of the above type in which, however, neither reference signal generator nor means for comparing the output of one of the sensors and the output of the reference signal generator are provided. In this apparatus, means are provided for varying the air flow through the sample, formed in particular by a battery of constant flow devices mounted in parallel, and connecting the sample holder to the pump. In series with each device is connected a valve and the nominal values of the flows likely to pass through each of the branches are in geometric progression: the first device, when it is operating, has necessarily passing therethrough a flow of 1 liter per minute, the second a flow of two liters per minute, the third a flow of four liters per minute and so on.

Now, in order to make measurements in compliance with the standard ISO 2965, each permeability measurement must be made under specified pressure differential conditions, for example 0.25 and 1 kilopascal.

The quantification of the flow rates which may be achieved with the known apparatus involve a quantification of the pressure differential which does not allow, except by chance, to repeat materially the preceeding pressure differential conditions. It is therefore necessary, with this system, to seek combinations of constant flow devices such that the corresponding measured pressure differential bracket the specified value as closely as possible. The permeability for this specified value is then obtained by an interpolation calculation from the measured values.

The result is a long and tiresome measuring operation, the result of which is impaired through an error related to the interpolation.

To overcome these drawbacks, the U.S. Pat. No. 4,311,037 provides a reference signal generator, means for comparing the output of one of the two sensors with the output of the reference signal generator and a pump with variable speed of rotation whose rotational speed is controlled by the output of the comparison means.

Thus, when such an apparatus is adapted, for example, so that the output of the sensor measuring the pressure differential is applied to the comparison means, it allows a constant pressure differential to be obtained permanently, whose value is equal to the specified value, by means of the reference signal generator.

However, such an apparatus can only respond slowly to relatively rapid variations at the output of the reference generator, because the regulation for obtaining a given flow, or a given pressure differential, is obtained by varying the rotational speed of the pump. This results in inaccuracies in the measurements when they must be made rapidly, or risks of having the whole apparatus self oscillating.

Furthermore, with the apparatus described in the U.S. Pat. No. 4,311,037, the testing of a large number of separate samples is long and tiresome, for it is necessary to stop the pump for each sample change and then to wait for a fairly long time until the pressure differential is reestablished.

Finally, in this apparatus, the measurement of the flow passing through the sample uses a venturi, i.e. a restriction in a pipe. Now, such a device has a non linear flow-pressure characteristic, which limits the use of the apparatus to a relatively narrow range of flow rates if it is desired to avoid tiresome corrections.

SUMMARY OF THE INVENTION

The present invention overcomes these disadvantages. It provides first of all an object of the above defined type further comprising a valve, inserted between said sample and said pump for controlling the flow rate, controlled continuously by the output of said comparison means.

In the apparatus of the invention, the variations of the pressure differential follow practically instantaneously those of the output signal of the comparison means. The response time of the system is therefore very short.

The measuring time is reduced to a minimum, for the pressure differential reaches the value specified by the operator by means of the reference signal generator in a very short time.

According to another feature of the invention, said comparison means comprise an electronic circuit, having a subtractor assembly followed by an amplification chain comprising a proportional response amplifier, an integral response amplifier and a derived response amplifier, these three amplifiers being connected in parallel, said chain being followed by a power amplifier for controlling said valve.

The accuracy of the system is high, without any risk of self oscillation.

According to another feature of the invention, the apparatus comprises, inserted between said valve and said pump, a branch pipe connected to the atmosphere through an auxiliary valve for nulling said pressure differential when the pump remains in operation.

Changing samples may then be very rapid.

According to another feature of the apparatus of the invention, said flow rate sensor comprises a multicapillary pressure loss element and a differential pressure sensor.

The flow rate measurement is then linear over a very wide range of flow rates.

The apparatus of the invention may also be adapted so that the output of the sensor measuring the air flow is applied to the comparison means so that a particular flow rate value, specified by means of the reference signal generator, is produced, for example for complying with a different test recommendation of the above mentioned standards.

BRIEF DESCRIPTION OF THE DRAWINGS

The invention will be better understood from the following description of a preferred embodiment of the system of the invention, with reference to the accompanying drawings in which.

DESCRIPTION OF THE PREFERRED EMBODIMENTS

Figure 1:
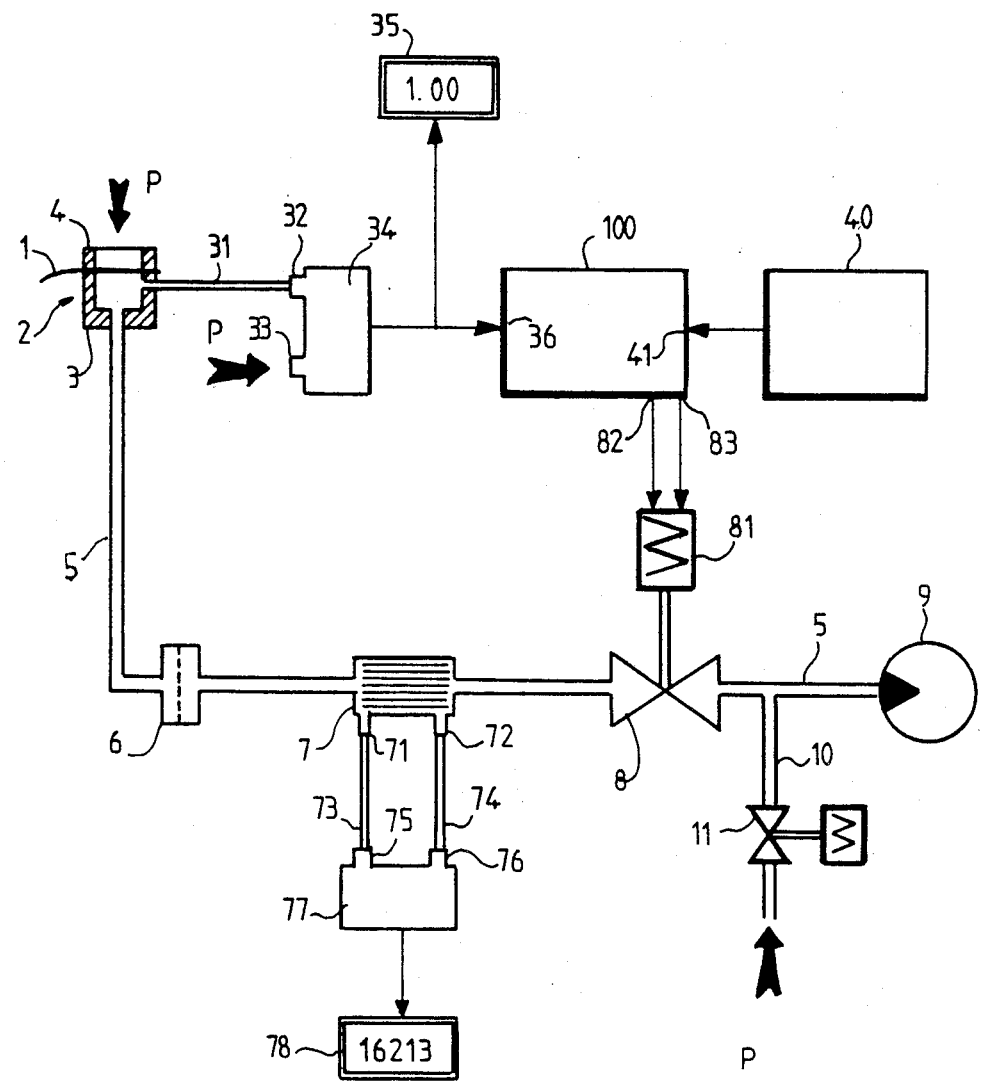
FIG. 1 shows a general diagram of the apparatus of the invention.

Referring to FIG. 1, a cigarette paper sample comprising an internal face and an external face and whose permeability it is desired to measure is placed in a sample holder 2. The sample holder 2 is formed of a fixed metal piece 3 open on one side and a mobile metal piece 4 open on both sides resting on the fixed piece 3 with, placed therebetween, a silicon elastomer seal so as not to deform or mark the sample which must be placed between the metal pieces 3 and 4. The metal pieces 3 and 4 define a measuring surface of given shape and dimensions. The external face of sample 1 is placed on the mobile piece 4 side which leaves it subjected to the atmospheric pressure P. The fixed piece 3 is in communication with a duct 5.

Duct 5 is connected to a pump 9 through a filter 6, a multicapillary pressure loss element 7 and a continuously controlled control valve 8.

The multicapillary pressure loss element 7 is provided with two outlets 71 and 72 connected by two ducts 73 and 74 to the inputs 75 and 76 of a differential pressure sensor 77 with electric output. This output is connected to an electronic display circuit 78.

A branch circuit 10 is connected to duct 5 between valve 8 and pump 9. The branch 10 is connected to the atmosphere through an auxiliary valve 11.

The fixed piece 3 is also in communication with the duct 31 connected to an input 32 of a differential pressure sensor 34 with electric output. The other input 33 of sensor 34 is subjected to the atmospheric pressure P. The electric output of sensor 34 is connected on the one hand to an electronic display circuit 35 and on the other to an input terminal 36 of an electronic valve control circuit 100.

The electric output of a reference signal generator 40, controllable by an operator, is connected to an input terminal 41 of the electronic valve control circuit 100. The coil 81 of the continuously controlled control valve 8 is connected to two outputs 82 and 83 of the electronic valve control circuit 100.

Figure 2:
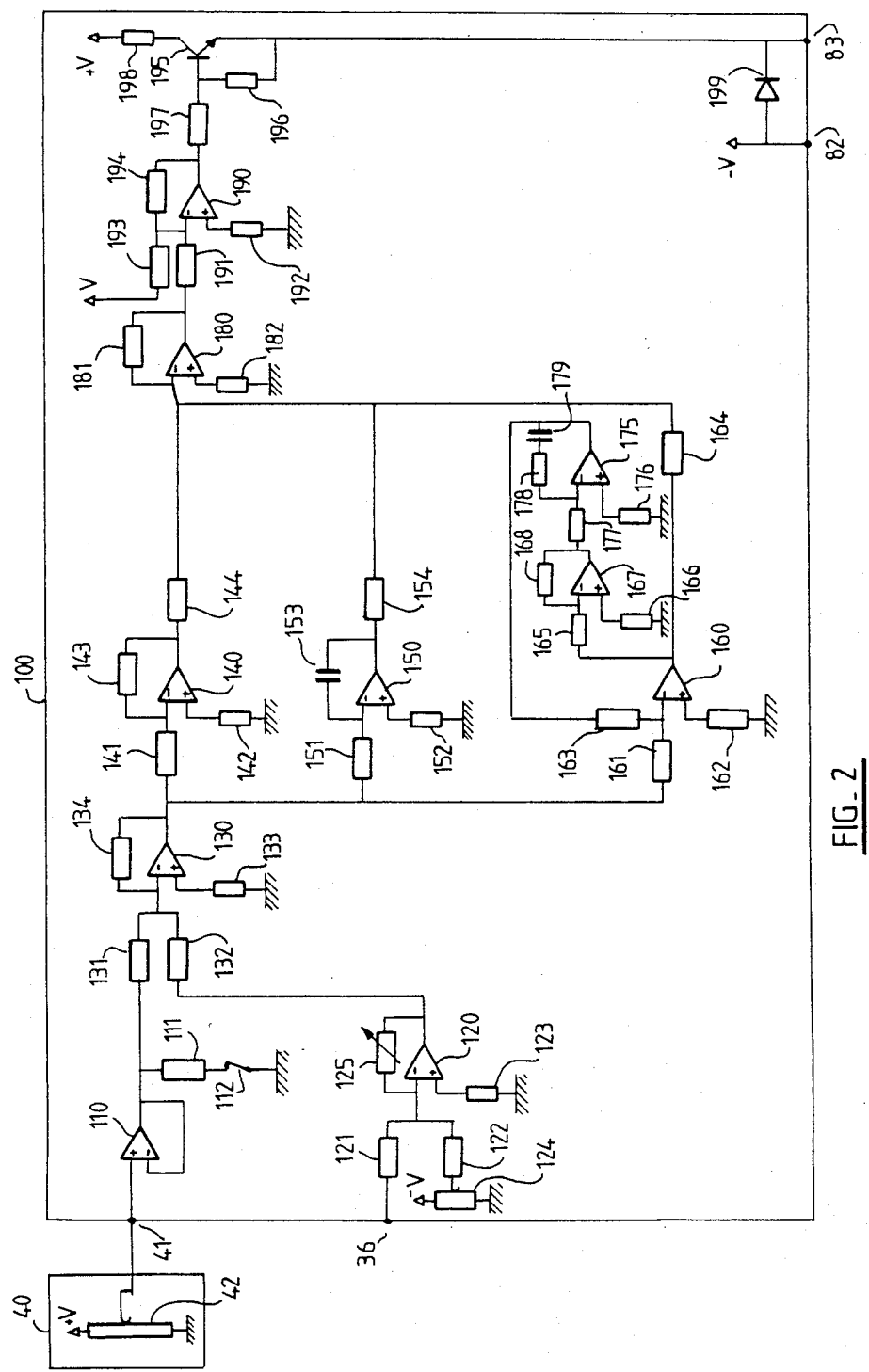
FIG. 2 shows a diagram of the electronic circuit controlling the valve and the reference signal generator of FIG. 1.

Referring now to FIg. 2, the input terminal 41 is connected to the plus input of an operational amplifier, designated hereafter by O. A., 110 connected in a follower circuit, whose output is connected to ground through a relay contact 112 and a resistor 111 and to the minus input of an O.A. 130 through a resistor 131.

The input terminal 36 is connected by a resistor 121 to the minus input of an O.A. 120 whose plus input is grounded through a resistor 123. The slider of a potentiometer 124, whose ends are connected to ground and to a negative supply voltage $-V$, is connected to the minus input of O.A. 120 through a resistor 122. A potentiometer 125 is placed between the output and the minus input of the O.A. 120. The output signal of the O.A. 120 is connected to the minus input of O.A. 130 through a resistor 132.

The plus input of O.A. 130 is grounded through a resistor 133. A resistor 134 is placed between the minus input and the output of O.A. 130.

The output of O.A. 130 is connected to the minus inputs of three O.A.s 140, 150 and 160 through three resistors 141, 151 and 161 respectively. The plus inputs of the three O.A.s 140, 150 and 160 are grounded through three resistors 142, 152, 162, respectively. The outputs of the three O.A.s 140, 150, and 160 are connected to the minus input of an O.A. 180 through three resistors 144, 154, and 164 respectively.

A resistor 143 is placed between the minus input and the output of the O.A. 140.

A capacitor 153 is placed between the minus input and the output of the O.A. 150.

The minus input of O.A. 160 is connected to the output of an O.A. 175 through a resistor 163. A capacitor 179 in series with a resistor 178 is connected between the minus input and the output of the O.A. 175. The plus input of the O.A. 175 is grounded through a resistor 176.

A resistor 177 connects the output of an O.A. 167 to the minus input of the O.A. 175.

A resistor 168 is placed between the minus input and the output of the O.A. 167. A resistor 165 connects together the output of the O.A. 160 and the minus input of the O.A. 167. The plus input of the O.A. 167 is grounded through resistor 166.

The plus input of the O.A. 180 is grounded through a resistor 182. A resistor 181 connects together the minus input and the output of the O.A. 180. The output of O.A. 180 is connected to the minus input of an O.A. 190 through a resistor 191. A positive supply voltage V is connected to the minus input of O.A. 190 through a resistor 193. A resistor 194 connects together the minus input and the output of O.A. 190.

The output of O.A. 190 is connected to the base of a power transistor 195 through a resistor 197. The collector of the transistor 195 is connected to the positive supply voltage V through a resistor 198. A resistor 196 is connected in parallel across the emitter-base junction of transistor 195. The emitter of transistor 195 is connected to the output terminal 83. The output terminal 82 is connected to the negative supply voltage $-V$. A diode 199 connects together the terminals 82 and 83.

To simplify the Figure, the supply sources delivering the power supply voltages $+V$ and $-V$ have not been shown. They are of conventional design.

The reference signal generator 40 is formed by a potentiometer 42 whose ends are connected to ground and to the positive supply voltage V. The voltage on the mobile slider forms the reference signal applied to terminal 41.

The apparatus of the invention which has just been described operates as follows.

While the sample 1 is being placed on the sample holder 2, valve 8 is closed for contact 112 is open, which results in a zero reference value, and valve 11 is opened (by control electronics not shown) so as to ensure a zero pressure differential on the sample while allowing pump 9 to remain in operation.

When the sample is in position, the operator adjusts the reference signal generator 40 to a certain value applied to the terminal 41 of circuit 100. At the beginning of the measurement, the pressure differential to which the sample 1 is subjected is zero, and the signal applied to terminal 36 of circuit 100 is zero.

The circuit 100 operates in the following way. The O.A. 110 is connected as a follower and O.A. 120 as an inverter, shifter and level adapter. The result is that the output of the inverter-adder amplifier 130-134 varies as the difference between the signal representative of the measured pressure differential applied to terminal 36 and the reference signal applied to terminal 41. The output of amplifier 130-134 is applied to the input of the chain formed by the parallel connection of an inverter amplifier 140-144 with proportional response, an inverter amplifier 150-154 with integral response and an inverter amplifier 160-179 with derived response. The output of this chain is formed by the output from the adder inverter 180-182 and it controls, through the inverter-shifter and level adapter amplifier 190-194 a power stage 195-198 for driving the coil 81 of the continuously controlled control valve 8, which winding is protected by diode 199, in a direction such that the valve opens when the difference between the signal representative of the measured pressure differential and the reference signal is negative.

This is what happens at the beginning of measurement and the pressure differential then increases, valve 8 being open. It closes when the pressure differential reaches the value specified by the reference signal generator 40. The proportional, integral and derived response amplifiers 140-144, 150-154, 160-179 allow this state to be reached rapidly with the best speed-accuracy-stability compromise.

With the sample being subjected to the specified pressure differential, the flow rate may be measured through the multicapillary pressure loss element 7 whose pressure-flow rate characteristic is strictly linear, and the permeability of the sample can be calculated.

Filter 6 protects the multicapillary pressure loss element 7.

Figure 4:
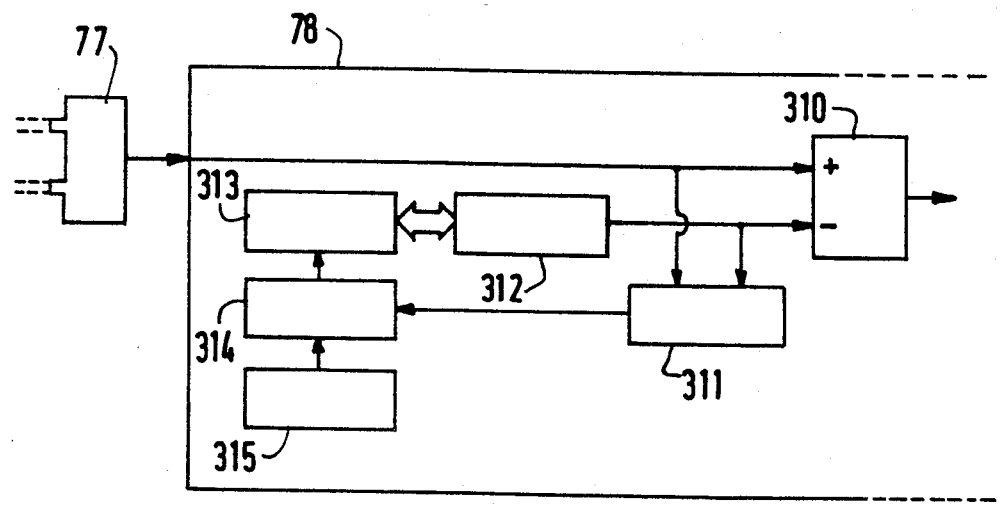
FIG. 4 shows a general diagram of the device for automatically resetting the flow rate measurement of the apparatus of FIG. 1.

So as to obtain good accuracy even with low flow rates, automatic resetting is provided before each measurement in the display system 78. In the moments preceding the measurement, the residual voltage present at the output of 77 is stored so as to be permanently subtracted subsequently from the raw result of the measurement. Storage is effected, as is shown in FIG. 4, by means of a clock pulse generator 315 which causes a counter 313 to advance, followed by a digital-analog converter 312 whose output voltage is compared with the residual voltage by a comparator 311, the clock pulses being blocked by a gate 314 when these two voltages are equal. At the output of the digital-analog converter 312 there is then available an analog voltage equal to the residual voltage just before the measurement, and which may be subtracted by an analog subtractor 310 from the raw result.

By way of example, the measurement time of an apparatus in accordance with the description is of the order of a second.

Figure 3:
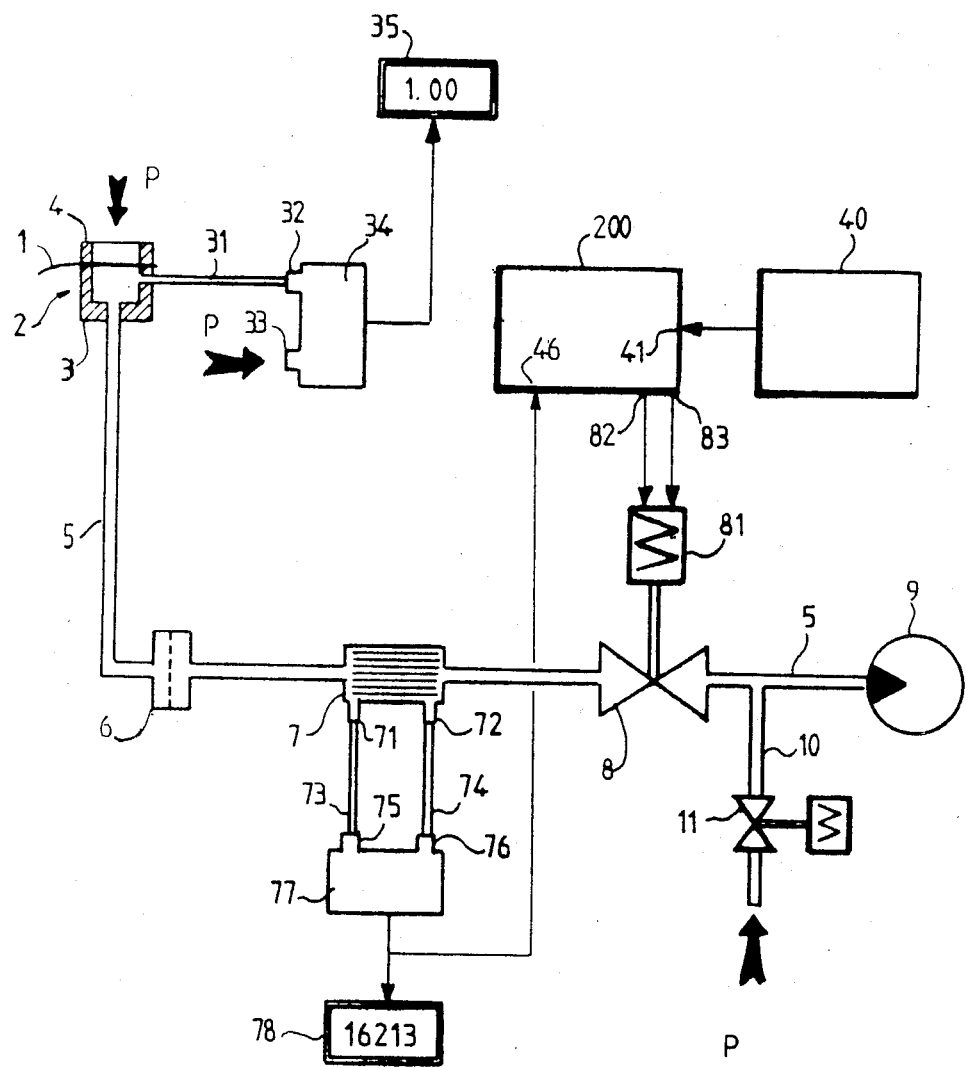
FIG. 3 shows a general diagram of a variant of the apparatus of the invention.

Finally, the preferred embodiment described above is not the only one possible, and FIG. 3 shows a variant in which the output signal of sensor 77, representative of the measured flow rate, is applied to an input 46 of an electronic circuit 200 similar in principle to the circuit 100, the rest of the system being unchanged. It then becomes possible to make measurements under flow conditions fixed by the reference signal generator 40.

The preceding description of an apparatus for measuring the air permeability of a cigarette paper sample is of course not limitative. Thus the apparatus of the invention may be applied to the measurement of the flow-pressure characteristics of a gas other than air, and in particular of a particle loaded gas such as smoke. The sample considered may for example be the filter of a cigarette. or a cigarette. The measurements may also be carried out under various conditions of pressure differential (constant, or following a given time variation law) or of flow rate, or else may concern the combustion speed of a cigarette under particular conditions. Finally, the apparatus of the invention is very well adapted to measurements of the continuous type in which the sample is a strip of great length which travels at a certain speed past the sample holder, which has been adequately transformed. The rapid response of the apparatus of the invention allows the variations of the characteristics of the sample to be accurately followed, even when it travels relatively quickly.

What is claimed is:

1. An apparatus for measuring the flow-pressure characteristics of a gas passing through a product sample with two faces, comprising a sample holder adapted so that one of the faces of the sample is subjected to atmospheric pressure, a pump for creating a pressure less than atospheric on the other face of the sample, a sensor for measuring the difference in pressures between said faces, a sensor for measuring the gas flow rate through the sample which results from said difference in pressure a reference signal generator and means for comparing the output of one of the two sensors with the output of the reference signal generator, and a valve inserted between said sample and said pump for controlling said flow rate, said valve being controlled continuously by the output of said comparison means.

2. The apparatus as claimed in claim 1, wherein said comparison means comprise an electronic circuit, including a subtractor assembly, followed by an amplification chain comprising a proportional response amplifier, an integral response amplifier and a derived response amplifier, these three amplifiers being connected in parallel, said chain being followed by a power amplifier for controlling said valve.

3. The apparatus as claimed in claim 1, further comprising, between said valve and said pump, a branch duct connected to the atmosphere through an auxiliary valve for nulling said difference in pressure when the pump remains in operation.

4. The apparatus as claimed in claim 1, wherein said flow rate sensor comprises a multicapillary pressure loss element and a differential pressure sensor.

5. The apparatus as claimed in claim 1, further comprising means for storing the value of the residual voltage at the output of the flow rate sensor and means for subtracting this value from the measured value.

6. The apparatus as claimed in claim 1, wherein the output of said reference signal generator is variable in time.

* * * * *